(12) United States Patent
Wagner et al.

(10) Patent No.: US 11,666,906 B2
(45) Date of Patent: Jun. 6, 2023

(54) PARTS FOR DIAGNOSTIC DEVICES

(71) Applicant: HEWLETT-PACKARD DEVELOPMENT COMPANY, L.P., Houston, TX (US)

(72) Inventors: Matthew J. Wagner, Palo Alto, CA (US); Donald Williams, Palo Alto, CA (US); Michele Huang, Singapore (SG); Rita Gozali, Singapore (SG); Sanjay Kumar Sinha, Singapore (SG); Barrett R. Crane, Ft. Collins, CO (US); Peter-P Zhang, Shanghai (CN); Doreen Ai Siang Chan, Singapore (SG)

(73) Assignee: Hewlett-Packard Development Company, L.P., Houston, TX (US)

( * ) Notice: Subject to any disclaimer, the term of this patent is extended or adjusted under 35 U.S.C. 154(b) by 1332 days.

(21) Appl. No.: 16/077,815

(22) PCT Filed: Jun. 30, 2017

(86) PCT No.: PCT/CN2017/091075
§ 371 (c)(1),
(2) Date: Aug. 14, 2018

(87) PCT Pub. No.: WO2019/000382
PCT Pub. Date: Jan. 3, 2019

(65) Prior Publication Data
US 2021/0197193 A1    Jul. 1, 2021

(51) Int. Cl.
*B01L 3/00* (2006.01)
*A61B 5/15* (2006.01)
(Continued)

(52) U.S. Cl.
CPC ........ *B01L 3/502715* (2013.01); *A61B 5/157* (2013.01); *A61B 5/150022* (2013.01);
(Continued)

(58) Field of Classification Search
CPC .. B01L 3/502715; B01L 3/5027; B01L 3/502; B01L 3/50; B01L 3/502746;
(Continued)

(56) References Cited

U.S. PATENT DOCUMENTS 6,066,243 A    5/2000   Anderson et al.
9,211,087 B2  12/2015  Hutchinson
(Continued)

FOREIGN PATENT DOCUMENTS

CN    1828307 A    9/2006
CN  103328963 A    9/2013
CN  103940817 A    7/2014

OTHER PUBLICATIONS

CN 1828307 A, Description English Machine Translation, obtained from https://worldwide.espacenet.com, May 26, 2022. (Year: 2022).*
(Continued)

*Primary Examiner* — Christine T Mui
(74) *Attorney, Agent, or Firm* — Foley & Lardner LLP

(57) ABSTRACT

In some examples, a diagnostic device includes a reusable part to receive a container of a fluid, the reusable part reusable for a plurality of diagnostic tests. The diagnostic device further includes a disposable part detachably attached to the reusable part and comprising a sample collector to collect a target sample of a living being. The diagnostic device further includes a tester comprising a fluid channel to transport the fluid to combine the fluid and the target sample to form a fluid combination, and to use the fluid combination to diagnose a condition of the target sample.

16 Claims, 10 Drawing Sheets

(51) Int. Cl.
  *A61B 5/157*   (2006.01)
  *B01L 7/00*    (2006.01)
  *G01N 1/10*    (2006.01)
  *A61B 5/145*   (2006.01)
  *A61B 10/00*   (2006.01)

(52) U.S. Cl.
  CPC .. *A61B 5/150267* (2013.01); *A61B 5/150343* (2013.01); *B01L 3/502746* (2013.01); *B01L 7/00* (2013.01); *G01N 1/10* (2013.01); *A61B 5/14532* (2013.01); *A61B 5/150412* (2013.01); *A61B 10/007* (2013.01); *A61B 10/0051* (2013.01); *A61B 2560/0214* (2013.01); *A61B 2560/0418* (2013.01); *B01L 2300/069* (2013.01); *B01L 2300/0816* (2013.01)

(58) Field of Classification Search
  CPC ............ B01L 7/00; B01L 2300/069; B01L 2300/0816; A61B 5/150022; A61B 5/150343; A61B 5/157; G01N 1/10
  USPC .............................................. 435/5; 422/500
  See application file for complete search history.

(56) References Cited

U.S. PATENT DOCUMENTS

| | | |
|---|---|---|
| 9,402,954 B1 | 8/2016 | Slevin |
| 2004/0176705 A1 | 9/2004 | Stevens |
| 2011/0313349 A1 | 12/2011 | Krulevitch et al. |
| 2013/0071944 A1 | 3/2013 | Ulrich et al. |
| 2014/0176705 A1 | 6/2014 | Ibamoto |
| 2017/0106371 A1* | 4/2017 | Athanasiou ............. B01L 3/502 |

OTHER PUBLICATIONS

Berger, "The Ideal Microfluidic Point-of-Care Device", Retrieved from internet—https://www.nanowerk.com/spotlight/spotid=21383.php, May 17, 2011, 5 Pages.

* cited by examiner

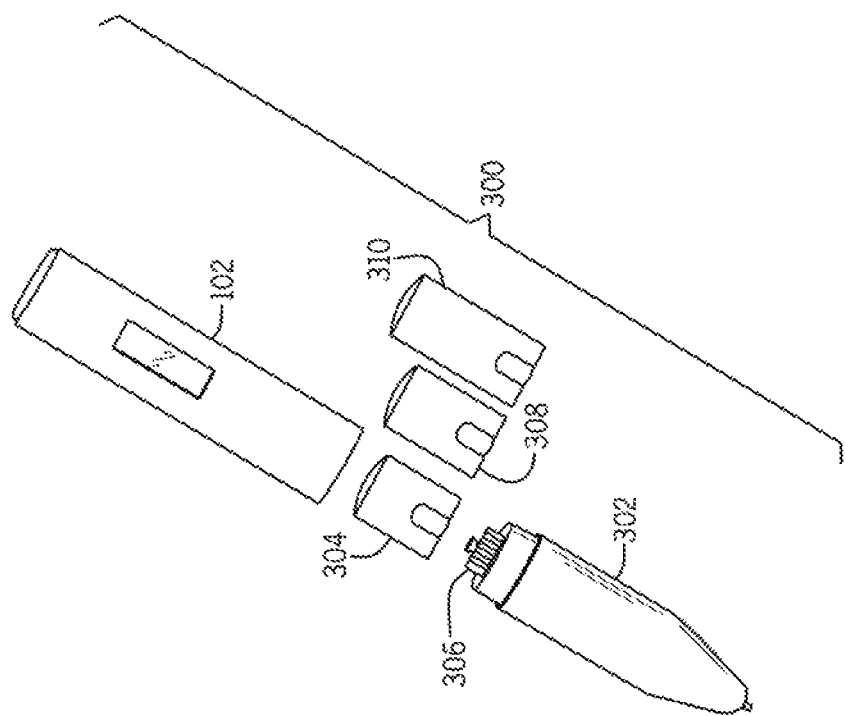
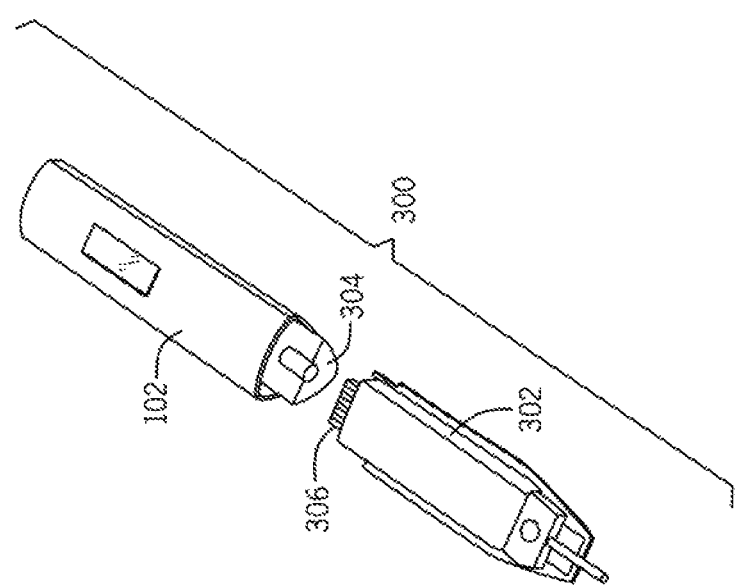
FIG. 3B
FIG. 3A

PARTS FOR DIAGNOSTIC DEVICES

BACKGROUND

Diagnostics of living beings can be performed based on collected biological samples. Examples of biological samples include blood, saliva, urine, mucus, skin, breath, and so forth. Diagnostics can be performed using various diagnostic devices.

BRIEF DESCRIPTION OF THE DRAWINGS

Some implementations of the present disclosure are described with respect to the following figures.

FIGS. 1A and 18 are block diagrams of diagnostic devices according to some examples.

FIGS. 3A and 3B illustrate exploded views of a diagnostic device, according to further examples.

Figure 1A:
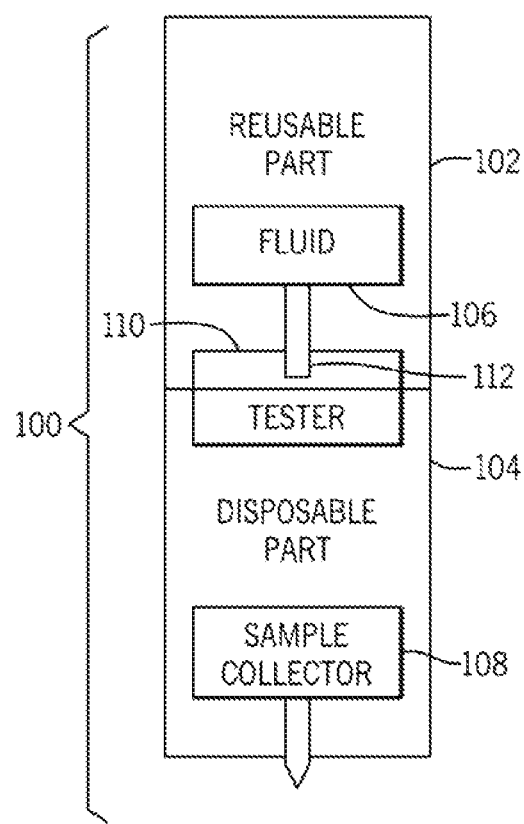

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

In the present disclosure, use of the term "a," "an", or "the" is intended to include the plural forms as well, unless the context clearly indicates otherwise. Also, the term "includes," "including," "comprises," "comprising," "have," or "having" when used in this disclosure specifies the presence of the stated elements, but do not preclude the presence or addition of other elements.

In some scenarios, diagnostic tests can be performed by sending biological samples of living beings to a test laboratory. Living beings can include humans, animals, or plants. Sending biological sample to a test laboratory can be a time consuming approach of preforming diagnostic tests, since it can take days for the biological samples to be transported to the test laboratory, and for the test laboratory to perform tests on the biological samples and provide reports of the tests.

In other examples, diagnostics of biological samples of living beings can be performed with single-use diagnostic devices, such as test strips (e.g., litmus papers), that are discarded after a single use. Although such single-use diagnostic devices can quickly diagnose certain health conditions (e.g., blood sugar level, etc.), the single-use diagnostic devices can be costly or can have limited capabilities or accuracy.

In further examples, complex diagnostic devices can be used at a point of care, such as at a doctor's office, at the location of a patient in a hospital, in a clinic, at a patient's home, in an assisted living facility, or at any other location of the patient. However, users of such complex diagnostic devices may have to be specially trained to be able to operate the diagnostic devices properly. Additionally, such complex diagnostic devices can be costly.

In ensuing discussion, reference is made to collecting and analyzing biological samples from humans. However, techniques or mechanisms according to some implementations can be applied for collecting and analyzing biological samples from other living beings.

Moreover, although reference is made to collecting and analyzing biological samples, it is noted that similar techniques and mechanisms can be applied to non-biological samples, such as non-living tissue, food, water, air, and so forth.

In accordance with some implementations of the present disclosure, as shown in FIG. 1A, a portable diagnostic device 100 that is usable at a point of care includes a reusable part 102 and a disposable part 104. The diagnostic device 100 can be of a relatively small size to make it easier to carry and handle the diagnostic device 100. For example, the diagnostic device 100 can have a generally slim profile, such as in the shape of a pen, so that a user of the diagnostic device 100 can easily hold it in one hand. In other examples, the diagnostic device 100 can have a different shape, such as a tubular shape, a rectangular shape, an oval or circular shape, or any other shape, including irregular shapes.

The reusable part 102 can receive a container 106 of fluid to be used as part of a diagnostic test. In some examples, the container 106 can be in the form of a replaceable cartridge. In response to use of the diagnostic device 100 that depletes the fluid in the container 106, a cartridge that currently installed in the reusable part 102 can be removed, and replaced with a new cartridge that contains a fresh supply of the fluid. In other examples, the container 106 of fluid can be fixedly mounted in the reusable part 102. If the fluid in the container 106 is depleted, a fresh supply of fluid can be injected or otherwise supplied into the container 106.

The reusable part 102 is reusable for multiple diagnostic tests. The fluid in the container 106 can include a reagent or a buffer, in some examples. A reagent is to chemically react with a biological sample. A buffer includes a fluid that can be combined with a target fluid (e.g., a reagent or a biological sample), without affecting the chemistry of the target fluid.

More generally, the reusable part 102 can include a container of an agent, where an agent can include a fluid or a solid. If the agent is a solid (such as a reagent in solid form), the solid agent can first be mixed with a fluid (such as a buffer) before the agent mixed with the fluid is used in a diagnostic test.

The disposable part 104 is detachably attached to the reusable part 102. The disposable part 104 includes a sample collector 108 to collect a biological sample. The disposable part 104 can be detached from the reusable part 102 after each use. The detached disposable part 104 can be discarded, and a new disposable part 104 can be attached to the reusable part 102 to perform another diagnostic test based on a further collected biological sample.

In further examples, the tester 110 can contain an internal fluid (a buffer and/or a reagent) independent of or in addition to the fluid in container 106. The fluid in container 106 and the internal fluid of the tester 110 may be used in any combination depending on the nature of the testing and contents of each part. In some cases, just the internal fluid can be used to perform a diagnostic test.

The diagnostic device 100 further includes a tester 110. The tester 110 is shown as spanning both the reusable part 102 and the disposable part 104 in the example of FIG. 1A, to indicate that the tester 110 can include component(s) in the reusable part 102 and component(s) in the disposable part 104. In other examples, the tester 110 can reside completely within the disposable part 104, or can reside completely within the reusable part 102.

The tester 110 includes a fluid channel 112 to transport the fluid in the container 106 in the reusable part 102 to combine the fluid with the biological sample collected by the sample collector 108. Combining the fluid and the biological sample forms a fluid combination. In some examples, combining the fluid and the biological sample can refer to mixing the fluid and the biological sample, in which case a fluid mixture of the fluid and the biological sample is formed without chemically combining the fluid and the biological sample. An example of such a mixture is a mixture of a buffer and the biological sample.

In other examples, combining the fluid and the biological sample can refer to chemically combining the fluid and biological sample, such as when a reagent reacts with the biological sample. Thus, a "fluid combination" can refer to either a mixture of at least two source fluids, or a chemically combination of at least two source fluids.

The tester 110 uses the fluid combination to diagnose a health condition. Diagnosing a health condition can refer to any or some combination of the following: measuring a parameter associated with the biological sample (e.g., blood sugar level in a blood sample, a level of cholesterol in a blood sample, a level of a drug, alcohol, or other chemical in the biological sample, presence of an infectious agent, such as a virus, a bacteria, a fungus, in the biological sample, presence of a biological agent indicating pregnancy or fertility, presence of a marker indicating a tumor, and so forth. Examples of biological samples can include any or some combination of the following: blood, saliva, urine, mucus, skin, breath, and so forth.

More generally, in further examples, the tester 110 can be used to diagnose a condition of any type of target sample that can be collected by the sample collector 108, whether a biological sample or a non-biological sample such as food, water, and so forth. Diagnosing a condition of a target sample can refer to determining whether the target sample is exhibiting a specified characteristic (e.g., a pollutant level of water is above or below a threshold, a contaminant level of food is above or below a threshold, etc.).

The following examples refer to diagnostic devices used to diagnose biological samples. However, the diagnostic devices can also be applied to other types of samples.

As discussed further below, the tester 110 can include fluid channels to transport the fluid of the container 106, a chamber in which multiple fluids can be combined, and a controller (e.g., a microcontroller or other hardware processing circuit) that can perform a diagnostic test based on a measurement of a fluid combination formed in the chamber.

Although FIG. 1A shows that the reusable part 102 has just one container 106, the reusable part 102 can include multiple containers of fluids in other examples. The multiple containers (whether replaceable containers such as replaceable cartridges or fixed containers) can include different types of fluids, e.g., different types of reagents and/or buffers. The different types of fluids in the multiple containers can be used to perform multiple different diagnostic tests on a biological sample.

Integrating the reusable part 102 (including the container 106 of fluid) with the disposable part 104 (including the sample collector 108) into a diagnostic device that has a small profile enhances ease of use. Also, the diagnostic device 100 is a relatively simple device such that specialized training does not have to be performed for users of the diagnostic device.

Since the container 106 of fluid and the sample collector 108 are integrated into a single device when the reusable part 102 and the disposable part 104 are attached together, the amount of the fluid in the container 106 used in a diagnostic test can be precisely controlled by the tester 110 to avoid waste of the fluid. In examples where the fluid in the container 106 is a reagent, the reagent can be relatively costly, such that avoiding waste of the reagent can help to reduce costs associated with performing diagnostic tests.

Figure 1B:
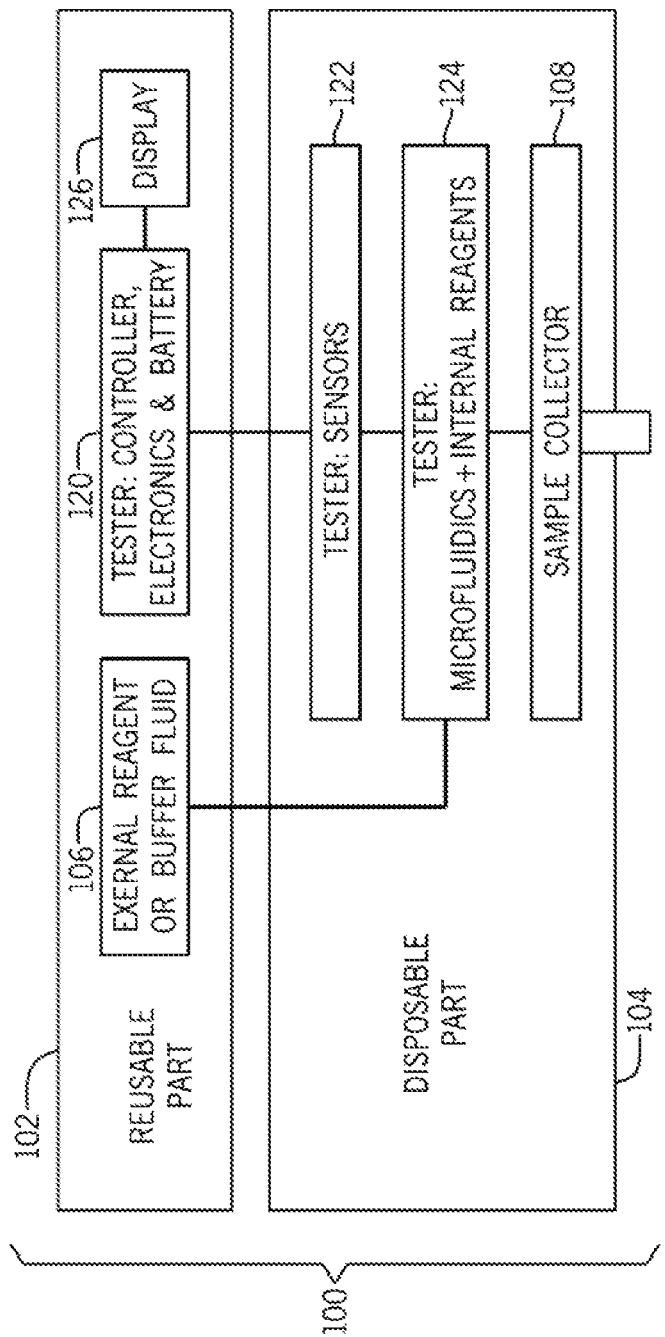

FIG. 1B illustrates the diagnostic device 100 according to further examples, to show further examples of what can be included in the tester 110 of FIG. 1A. The tester 110 can include a controller, other electronics, and a battery (represented as 120) in the reusable part 102. The controller 120 can control display of information in a display 126 of the reusable part 102. The tester 110 can further include sensors 122 and microfluidics (in the form of channels and mixing chambers) as well as any internal reagents (or other fluids) (represented generally as 124) in the disposable part 104.

Although FIG. 1B shows specific example components of the tester 110 in the reusable part 102 and the disposable part 104, it is noted that in other examples, the tester 110 can include other arrangements of components in the reusable part 102 and/or the disposable part 104.

Figure 2A:
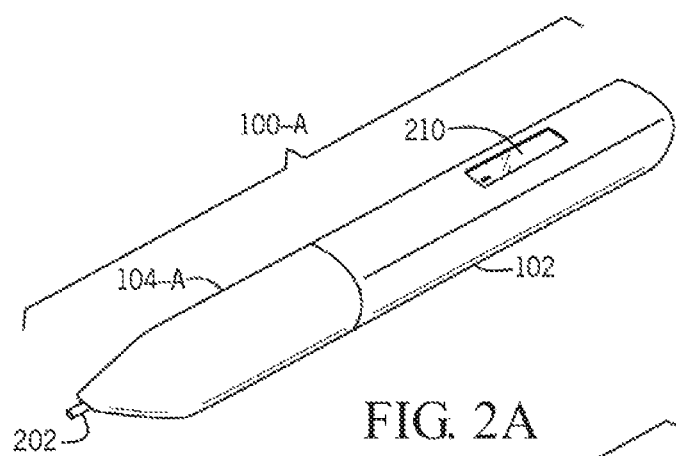
FIGS. 2A-2C illustrate different modular arrangements of diagnostic devices, according to various examples.
Figure 2B:
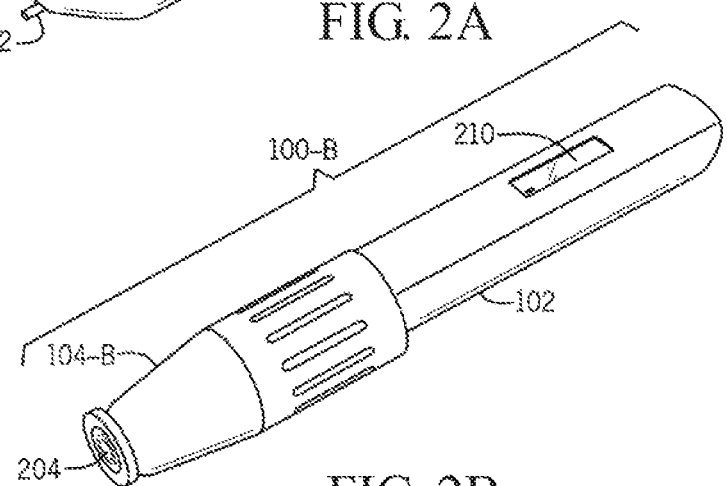
Figure 2C:
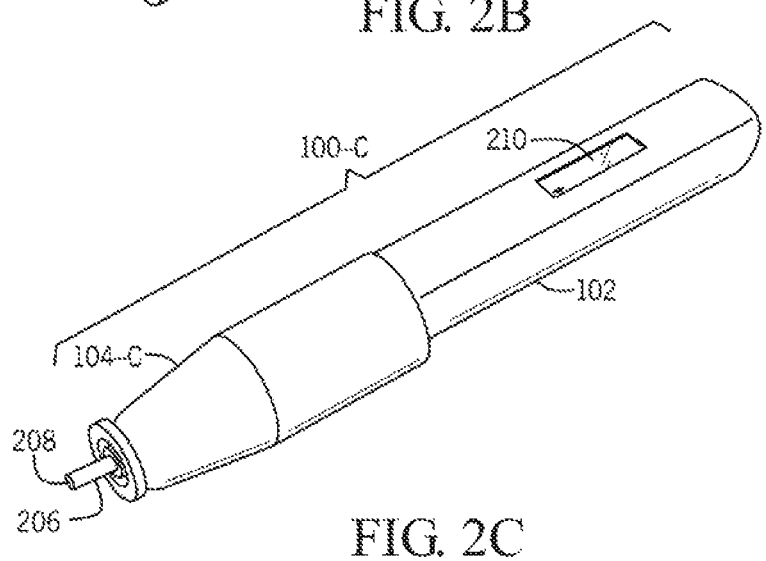

FIGS. 2A-2C illustrate three example diagnostic devices 100-A, 100-B, and 100-C, respectively. Each of the diagnostic devices 100-A, 100-B, and 100-C includes the reusable part 102. However, the diagnostic devices 100-A, 100-B, and 100-C use three different disposable parts 104-A, 104-B, and 104-C, where each of disposable part 104-A, 104-B, or 104-C is detachably attached to the reusable part 102. A user can successively attach the disposable parts 104-A, 104-B, and 104-C to the reusable part 102 to perform successive different diagnostic tests based on different biological samples collected by the disposable parts 104-A, 104-B, and 104-C, whether on the same patient or on different patients.

As used here, a "patient" can refer to a person on which a diagnostic test is to be performed. The patient can be under the care of a health professional, or the patient can simply be self-administering the diagnostic tests without being under the care of a health professional. In some examples, the patient can use the diagnostic device to perform a self-diagnosis—in such examples, the patient and the user of the diagnostic device is the same person. In other examples, a health professional or other person can use the diagnostic device to perform diagnostic tests on the patient.

In some examples, the disposable part 104-A is used to collect a blood sample, such as by inserting a lance or needle 202 through a skin of a patient to draw a blood sample from the patient.

The disposable part 104-B of FIG. 2B can be used to collect a breath sample of a patient through an input port 204. When the patient exhales, either through the patient's nose or mouth, the exhaled breath can be passed through the input opening 204 of the disposable part 104-B for collection inside the disposable part 104-B.

The disposable part 104-C of FIG. 2C includes a tube 206 with an opening 208 at the end of the tube 206. The opening 208 can be used to draw a fluid from the user, such as saliva in the user's mouth, urine from a container that contains urine and so forth.

In other examples, other types of disposable parts can be used in conjunction with the reusable part 102, such as disposable parts to collect skin samples, mucus samples, and so forth.

As further shown in each of FIGS. 2A-2C, the reusable part 102 includes a display device 210. The display device 210 can be used to display a result of the diagnostic test. For example, the display device 210 can display a positive indication or a negative indication. The positive indication can indicate a positive result (e.g., the patient is pregnant, the patient's glucose level is in a normal range, etc.), or a negative indication (e.g., the patient is not pregnant, the patient's sugar level is outside a normal range, etc.).

In other examples, the display device 210 can present a numerical value, such as a blood sugar level, a cholesterol level, and so forth. In further examples, the display device 210 can display a message, which can inform the patient or the user of an action to be taken or a condition of the patient. A message can inform the patient or user that the test indicates a normal result (i.e., there is no issue with the patient's health), or can issue a message indicating that the patient is experiencing a health problem or providing an alert that the patient should visit a doctor or a hospital.

By being able to produce a digital result that can be displayed by the display device 210, a more robust indication of a health condition of the patient can be presented. In other examples, instead of displaying a result of a diagnostic test in the display device 210, a different type of output device can be used. For example, a speaker of the diagnostic device can be used to audibly present the result of the diagnostic test.

In other examples, the diagnostic device can include a communication interface to transmit information including the result of the diagnostic test to another device. For example, the communication interface can include a wireless interface to communicate wirelessly over a wireless network with a remote device, where the remote device can include a computer, a smartphone, a remote server, and so forth.

In other examples, diagnostics are not performed at the diagnostic device. Instead, once a fluid (or multiple fluids) is (are) combined with the biological sample to form a fluid combination, a sensor (or multiple sensors) in the diagnostic device (where the sensor(s) can be part of the tester 110 of FIG. 1, for example) can be used to make a measurement (or multiple measurements) of the fluid combination. The measurement(s) can be sent by the communication interface to a remote device to apply analytics on the measurement(s). Offloading the analytic(s) to the remote device can leverage the processing resource of the remote device, such that the diagnostic device can be designed to be simpler and thus less costly (such as by not including a high-powered processor or microcontroller in the diagnostic device).

In some examples, the analytics performed by the remote device can be compared to historical diagnostic data (of the same patient or of multiple patients) to use the historical diagnostic data to aid in performing a diagnosis of a health condition of the target patient.

Once the analytics of a diagnostic test have been performed at the remote device, the result of the diagnostic test can be displayed at the remote device, or can be provided back to the diagnostic device for display by the diagnostic device.

The modular design of the diagnostic device that allows different reusable parts to be used with the reusable part allows for a wider variety of diagnostic tests to be performed with the diagnostic device than available in traditional simple diagnostic devices, such as test strips.

FIG. 3A shows another example diagnostic device 300, which includes a reusable part 102 and a disposable part 302 that has been detached from the reusable part 102. As depicted in FIG. 3A, a replaceable cartridge 304 (which is an example of the container 106 of fluid in FIG. 1) is inserted into the reusable part 102. FIG. 3A also shows a connector 306 that protrudes from one end of the disposable part 302. The connector 306 is to establish a connection with a corresponding connector (now shown) of the reusable part 102. In some examples, the connector 306 can include electrical contacts to establish an electrical connection between the disposable part 302 and the reusable part 102. The connector 306 can also include a fluid connector to allow for a fluid connection to be established between the disposable part 302 and the reusable part 102. This fluid connection allows the fluid contained in the cartridge 304 to be transported to the disposable part 302 (in examples where a tester is part of the disposable part 302). Alternatively, the fluid connection can allow for a biological sample collected by the disposable part 302 to be transported to the reusable part 102, in examples where the reusable part 102 includes a tester to test a fluid combination of the biological sample and the fluid from the cartridge 304.

FIG. 3B shows the cartridge 304 removed from the reusable part 102. Additionally, FIG. 3B shows additional cartridges 308 and 310 of sizes that differ from the size of the cartridge 304. A user of the diagnostic device 300 can insert any of the cartridges 304, 308, and 310 of respective different sizes into the reusable part 102, depending on the expected use of the diagnostic device 300. A larger cartridge can store more fluid than a smaller cartridge, and thus, can be reused a larger number of times.

As shown in FIG. 3B, the diagnostic device 300 has a modular design that is made up of multiple modules. In this manner, a cartridge of one of several different sizes can be selected for insertion into the reusable part 102. Additionally, any of different cartridges that store different fluids (e.g., different reagents and/or buffers) can be selected for insertion into the reusable part 102, depending on the diagnostic test desired. Moreover, any one of multiple different disposable parts can be selected for attachment to the reusable part 102, where the different disposable parts (such as those depicted in FIGS. 2A-2C) can collect different biological samples.

Figure 4:
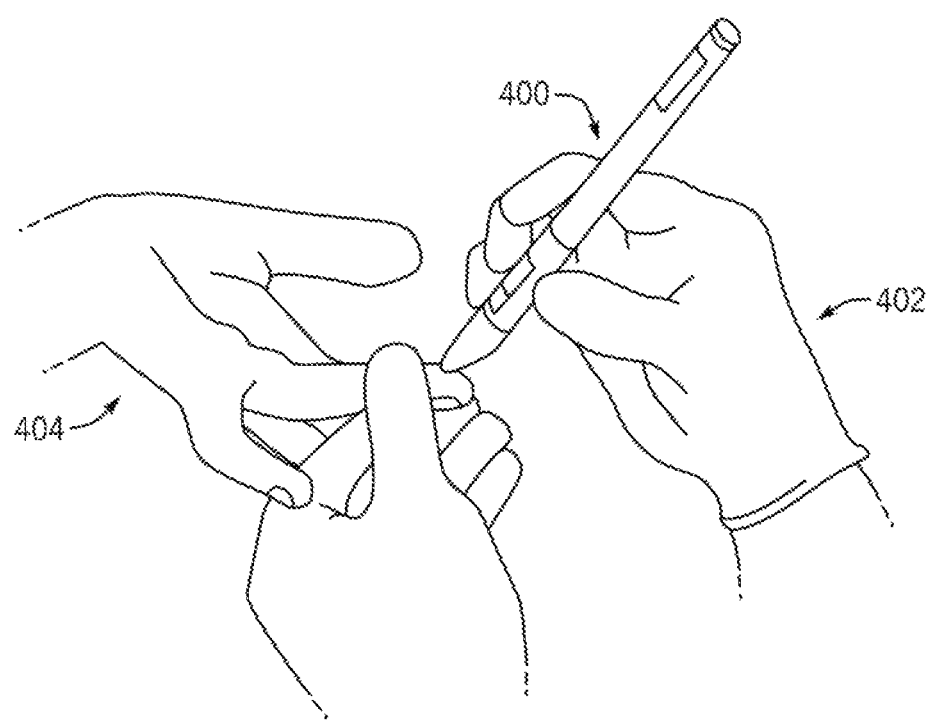
FIGS. 4 and 5A-5B illustrate operations of performing diagnostic tests according to some examples.

FIG. 4 shows one example of use of a diagnostic device 400, which can be similar to any of the diagnostic devices 100, 100-A, 100-B, 100-C, or 300 shown in FIGS. 1-3B. In the example of FIG. 4, a user (e.g., a health professional or other person) 402 grips the diagnostic device 400 with the user's hand. The lower tip of the diagnostic device 400 is engaged to prick a finger of a patient's hand 404, which initiates a flow of blood that can be drawn by capillary flow into a sample collector of the diagnostic device 400. To initiate the diagnostic test, the user 402 can press an activate button on the diagnostic device 400, which starts the sample collection process. Once the sample collection process is started, the diagnostic device 400 can continue to perform the diagnostic test automatically. Alternatively, the diagnostic device 400 can include another activation button that is to be pressed by the user 402 to initiate the diagnostic test after the biological sample has been collected from the patient's hand 404.

Figure 5B:
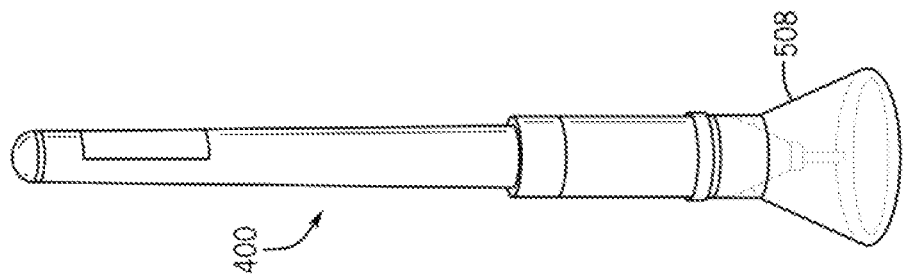
Figure 5A:
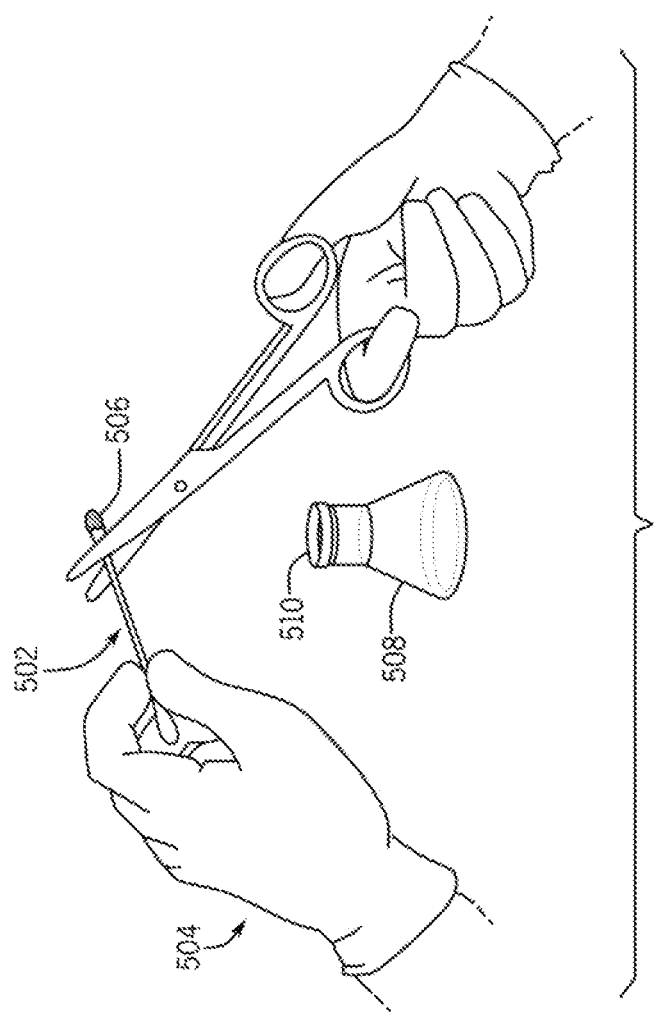

FIGS. 5A and 5B illustrate another example of performing a diagnostic test. FIG. 5A shows a swab 502 that has been used to swab a patient, such as in the patient's mouth to collect a mucus sample, or on the patient's skin to collect a skin sample, and so forth. A user (e.g., a health professional or other person) 504 can cut the swab 502 to remove a tip portion 506 of the swab 502, where the tip portion 506 has the collected biological sample. The tip portion 506 can be dropped into a flask 508 or other type of chamber.

With the tip portion 506 in the flask 508, the diagnostic device 400 can be inserted through an upper opening 510 of the flask 508, as shown in FIG. 5B. Once the diagnostic device 400 has been inserted into the flask 508, the diagnostic device 400 can be activated (such as by pressing a first control button) to cause a buffer to be ejected by the diagnostic device 400 into the flask 508. The buffer is mixed with the biological sample collected on the tip portion 506 in the flask 508.

The user can then activate the diagnostic device 400 (such as by pressing a second control button) to draw the mixture of the buffer and biological sample from the flask 508 and into the sample collector of the diagnostic device 400. Once drawn into the diagnostic device 400, a reagent in the diagnostic device 400 can be combined with the mixture of the buffer and biological sample. The fluid combination of the reagent, the buffer, and the biological sample can then be tested by the diagnostic device 400.

Figure 6A:
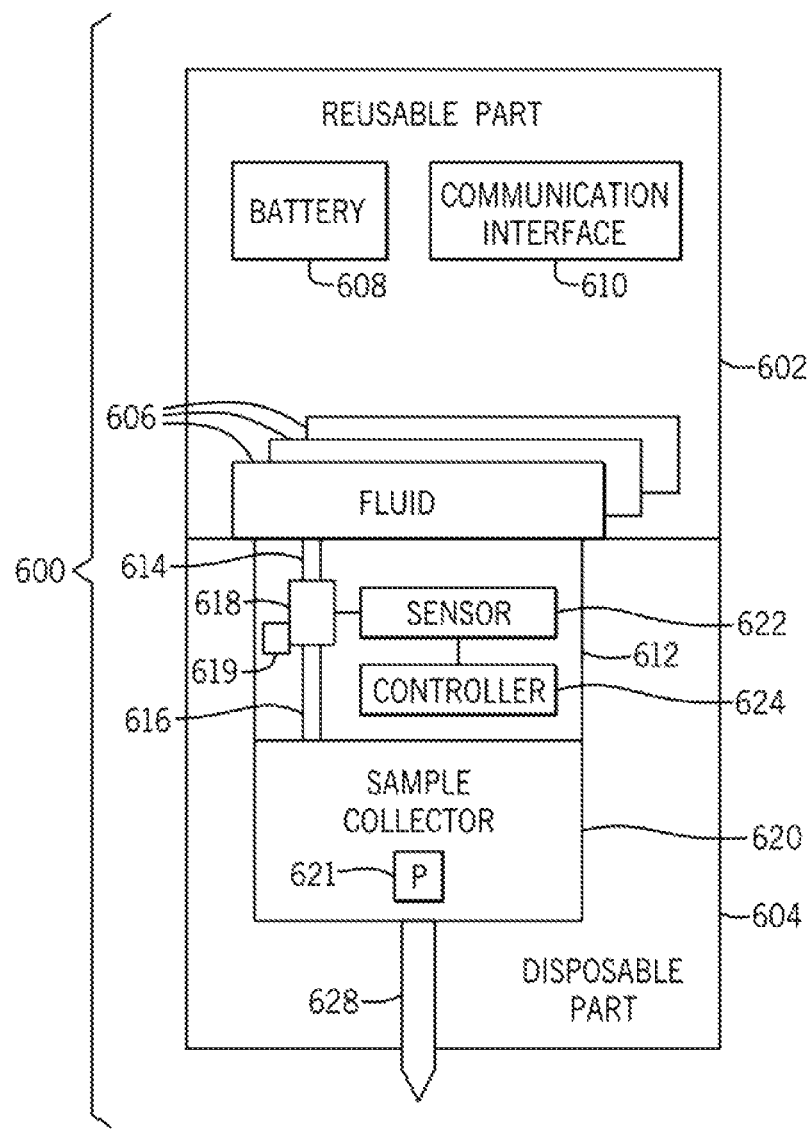
FIG. 6A is a block diagram of a diagnostic device according to further examples.

FIG. 6A is a block diagram of a diagnostic device 600 according to further examples. The diagnostic device 600 includes a reusable part 602 and a disposable part 604. The reusable part 602 includes a container 606 that contains a fluid, such as a reagent, or a buffer. In some examples, there can be multiple containers of different fluids in the reusable part 602. Each of the containers can be in the form of cartridges that are removably inserted into the reusable part 602.

The reusable part 602 includes a battery 608 and a communication interface 610. The battery 608 can be used to provide power to various components of the reusable part 602, as well as components in the disposable part 604 through an electrical connection between the reusable parts 602 and the disposable parts 604. The communication interface 610 allows the reusable part 602 to communicate with a remote device. In some examples, the communication interface 610 can include a wireless interface, such as a Wi-Fi interface, a cellular interface, a BLUETOOTH interface, and so forth. In other examples, the communication interface 610 can perform communications over a wired link.

The disposable part 604 includes an integrated circuit (IC) chip 612, which can be in the form of a die (e.g., a semiconductor die) or a circuit board. The chip 612 is an example of the tester 110 of FIG. 1. The chip 612 can include microfluidic channels 614 and 616. A microfluidic channel can refer to any channel that has a diameter or other cross-sectional size in the micrometer range (e.g., 1 to 999 micrometers) or nanometer range (e.g., 1 to 999 nanometers). The microfluidic channel 614 can transport fluid from one of the containers 606 to a fluid combination chamber 618. The microfluidic channel 616 can transport the biological sample collected by a sample collector 620 into the fluid combination chamber 618. The transport of a fluid from a container 606 and the biological sample from the sample collector 620 can be accomplished using respective fluid pumps, which can be part of the IC chip 612 or separate from the IC chip 612. In the example of FIG. 6A, a pump 621 is shown as being part of the sample collector 621 to pump a biological sample to the sample collector 620. The pump can include a thin film pump or a shape memory allow diaphragm pump. Similar types of pumps can be used to induce flow from a container 606.

In some examples, the chip 612 can further include a heater 619, which can be in the form of a thermal resistor, for example. When an electrical current is passed through the thermal resistor, the thermal resistor heats up. The heater 619 is placed adjacent the fluid combination chamber 618. When activated, the heater 619 heats a fluid combination in the fluid combination chamber 618. The heated fluid combination can then be applied in a diagnostic test.

In other examples, the heater 619 can be omitted.

The fluid and the biological sample can be combined in the fluid combination chamber 618. A sensor 622, which can also be part of the chip 612, can be used to measure a characteristic of the fluid combination. In other examples, multiple sensors can be provided to measure respective different characteristics of the fluid combination.

In further examples, one of the containers 606 can be in the form of a pack of a reagent in solid form. Another container 606 can contain a buffer. The pack can be punctured (such as by using an automatically actuated needle in the reusable part or by a needle applied by a user). The reagent in solid form can be mixed with the buffer to provide a liquid mixture, and the chip 612 can combine the liquid mixture with the biological sample to form a fluid combination for testing.

A controller 624, which can also be part of the chip 612, can be used to process the measurement made by the sensor 622 (or measurements made by multiple sensors), to determine a health condition. The controller 624 can be implemented as a hardware processing circuit (e.g., a microcontroller, a microprocessor, a core of a multi-core microprocessor, a programmable gate array, an programmable integrated circuit device, etc.), or as a combination of a hardware processing circuit and machine-readable instructions executable on the hardware processing circuit. The machine-readable instructions can be stored on a non-transitory machine-readable or computer-readable storage medium.

Although FIG. 6 shows an example where the controller 624 is part of the disposable part 604, in other examples, the controller 624 can be part of the reusable part 602.

In further examples, instead of performing a diagnostic test analysis using the controller 624 in the diagnostic device 600, the measurement(s) from the sensor(s) 622 can be transmitted by the communication interface 610 to a remote device, to perform the diagnostic test analysis at the remote device.

The disposable part 604 further includes a fluid channel 628, where a tip of the fluid channel 628 is sharp to prick through a patient's skin. Blood can be drawn through the fluid channel 628 for collection by the sample collector 620. In other examples, the fluid channel 628 can collect a different biological sample.

Although not shown, the battery 608 can be connected to a charging circuit, which can be charged when the reusable part 602 is either electrically connected to a power source (e.g., the AC wall outlet) or the reusable part 602 is placed in a power charging cradle for charging by inductive coupling.

Figure 6B:
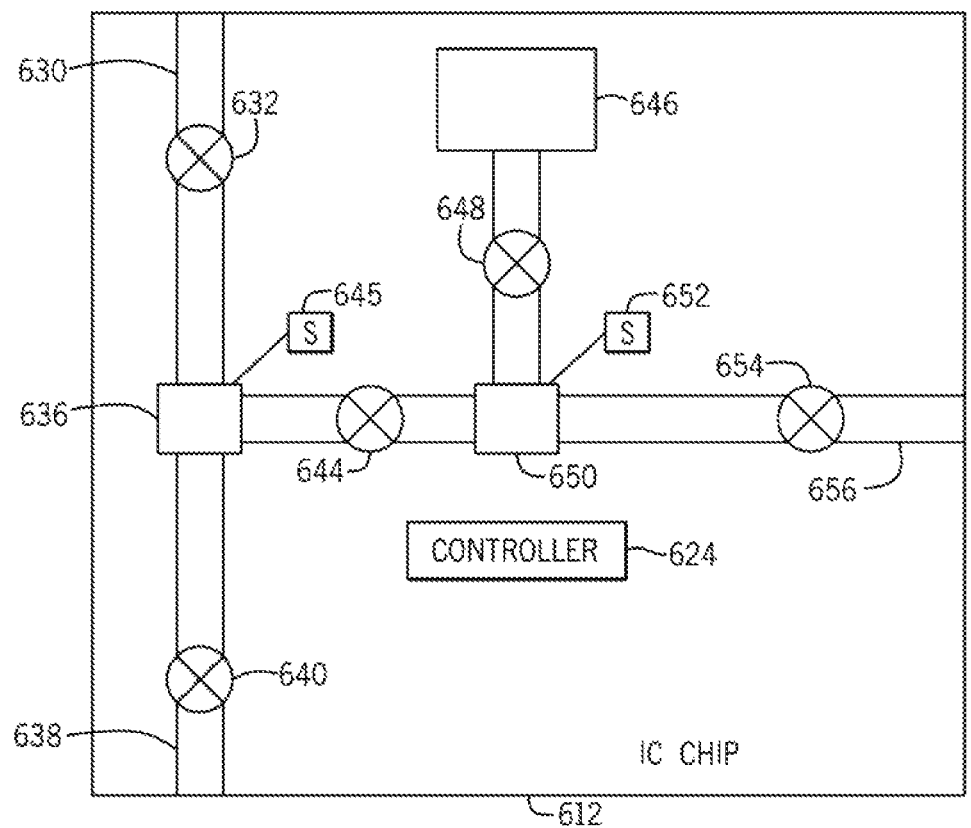
FIG. 6B is a block diagram of an integrated circuit (IC) chip useable in a diagnostic device according to further examples.

FIG. 6B shows further components inside the IC chip 612 according to further examples. The components include microfluidic channels, valves, sensors, and microfluidic chambers. A microfluidic channel 630 can transport fluid from a container 606 (FIG. 6A) of the reusable part 602. Fluid flow in the microfluidic channel 630 is controlled by a valve 632, which can be electronically controlled by the controller 624. When the valve 632 is open, fluid can flow in the microfluidic channel 630 through the valve 632 to a microfluidic chamber 636.

A microfluidic channel 638 can transport a target sample from the sample collector 620 (FIG. 6A) of the disposable part 602. Fluid flow in the microfluidic channel 638 is controlled by a valve 640, which can be electronically controlled by the controller 624. When the valve 640 is open, fluid can flow in the microfluidic channel 638 through the valve 640 to the microfluidic chamber 636, where the fluid from the container 606 is combined with the target sample.

A sensor 645 can be used to detect a characteristic of the combined fluid and target sample. Fluid from the microfluidic chamber 636 can flow through a valve 644 (if open as controlled by the controller 624) to another microfluidic chamber 650. In the example of FIG. 68, the IC chip 612 further incudes an internal container 646 that includes an internal fluid (reagent or buffer) that can be used in a diagnostic test. Fluid from the internal container 646 can be passed through a valve 648 (if open as controlled by the controller 624) to the microfluidic chamber 650, where the internal fluid is combined with the fluid combination of the fluid from the container 606 and the target sample.

A sensor 652 can measure a characteristic of the combined fluids in the chamber 650.

An output valve 654 is also provided. When the output valve 654 is closed, fluid can remain in the chamber 650. However, if the controller 624 opens the output valve 654, then the fluid in the microfluidic chamber 650 can be flowed to another location, such as to an output port of the IC chip 612 or to another chamber.

Figure 7:
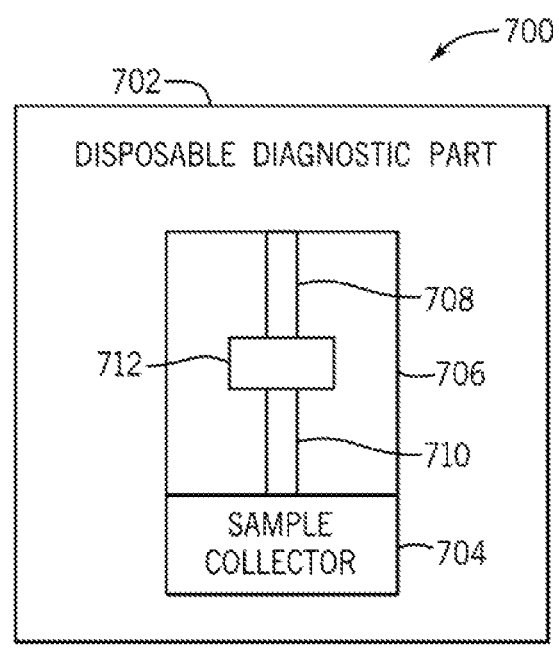
FIG. 7 is a block diagram of a disposable diagnostic part, according to alternative examples.

FIG. 7 is a block diagram of a disposable diagnostic part 700, which can be any of the disposable parts discussed above. The disposable diagnostic part 700 includes a housing 702 that detachably attaches to a reusable part of a diagnostic device, where the reusable part includes a fluid (or more generally, an agent). The disposable diagnostic part 700 includes a sample collector 704 that collects a biological sample. The disposable diagnostic part 700 further includes an IC chip 706 including a microfluidic channel 708 to transport the fluid in the reusable part, and a microfluidic channel 710 to transport the biological sample in the sample collector 704. The microfluidic channels 708 and 710 transport the fluid and the biological sample to a fluid combination chamber 712, where the fluid and the biological sample are combined to perform a diagnostic test.

Figure 8:
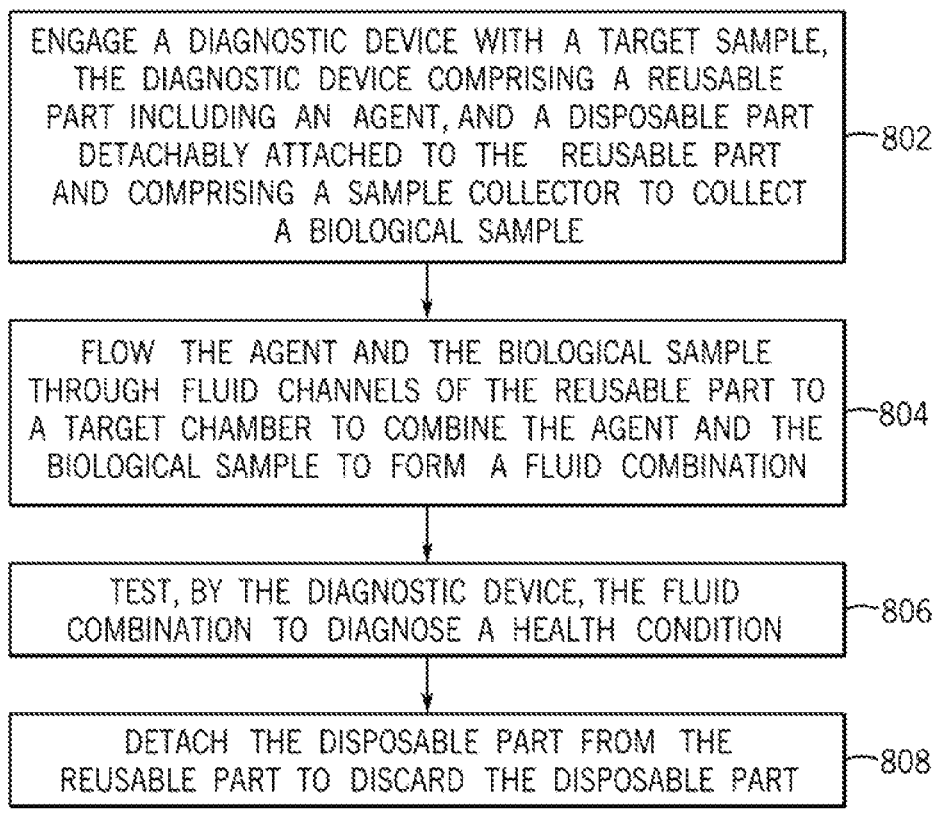
FIG. 8 is a flow diagram of a diagnostic test process according to some examples.

FIG. 8 is a flow diagram of a diagnostic test process applied to a living being. In other examples, the diagnostic test process can similarly be applied to a non-living entity. The diagnostic test process includes engaging (at 802) a diagnostic device with a target sample, the diagnostic device comprising a reusable part including an agent, and a disposable part detachably attached to the reusable part and comprising a sample collector to collect a biological sample of the living being.

The diagnostic test includes flowing (at 804) the agent and the biological sample through fluid channels of the reusable part to a target chamber to combine the agent and the biological sample to form a fluid combination. If the agent is initially in solid form, the agent can first be mixed with a buffer or other fluid, and the agent mixed with the fluid is then flowed to the target chamber to combine with the biological sample to form the fluid combination.

The diagnostic test includes testing (at 806), by the diagnostic device, the fluid combination to diagnose a health condition.

The diagnostic test further includes detaching (at 808) the disposable part from the reusable part to discard the disposable part.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

The invention claimed is:

1. A diagnostic device comprising: a reusable part to receive a container of an agent, the reusable part reusable for a plurality of diagnostic tests; a disposable part detachably attached to the reusable part and comprising a sample collector to collect a target sample; a tester comprising a channel to transport the agent to combine the agent and the target sample to form a fluid combination, and to use the fluid combination to diagnose a condition of the target sample; and a pack of a reagent in solid form, wherein the pack when punctured allows for mixing of the reagent and agent to provide a liquid mixture, and wherein the tester is to combine the liquid mixture with the target sample to form the fluid combination.

2. The diagnostic device of claim 1, wherein the agent comprises a buffer, and, wherein the pack when punctured allows for mixing of the reagent and the buffer to provide the liquid mixture.

3. The diagnostic device of claim 1, wherein the tester comprises a chip comprising microfluidic channels through which the target sample and the agent are able to flow, the chip to draw the agent from the container and the target sample from the sample collector.

4. The diagnostic device of claim 3, wherein the chip is part of the disposable part.

5. The diagnostic device of claim 3, wherein the tester further comprises a controller to perform the diagnosing of the condition based on a measurement of the fluid combination.

6. The diagnostic device of claim 5, wherein the controller is part of the reusable part or the disposable part.

7. The diagnostic device of claim 1, wherein the agent comprises a reagent.

8. The diagnostic device of claim 1, wherein the agent comprises a buffer.

9. The diagnostic device of claim 8, wherein the reusable part is to further receive a container including a second reagent, wherein the tester is to mix the buffer and the target sample by ejecting the buffer into a chamber that contains the target sample, to produce a mixture of the buffer and the target sample, wherein the sample collector is to draw the mixture of the buffer and the target sample from the chamber, and wherein the tester is to further: combine the mixture of the buffer and the target sample with the second reagent to form a fluid combination of the buffer, the target sample, and the second reagent, and test the fluid combination of the buffer, the target sample, and the second reagent to diagnose the condition.

10. The diagnostic device of claim 1, wherein the agent in the reusable part comprises a first reagent, and the tester is to perform a first type of diagnostic test of a fluid combination of the target sample and the first reagent, and wherein:

the reusable part further includes a second reagent different from the first reagent, and the tester is to mix the second reagent and the target sample to form a second mixture, and to use the second mixture to perform a second type of diagnostic test different from the first type of diagnostic test.

11. The diagnostic device of claim 1, wherein the tester comprises a heater to heat the fluid combination of the agent and the target sample.

12. The diagnostic device of claim 1, wherein the container of agent is a container of liquid agent that is fluidly connected by the reusable part to the tester.

13. The diagnostic device of claim 1, wherein the container of agent is removable from the reusable part.

14. The diagnostic device of claim 1, wherein the container of agent comprises a replaceable cartridge.

15. The diagnostic device of claim 1, wherein the reusable part is reusable for a plurality of diagnostic tests on different target samples.

16. A diagnostic device comprising: a reusable part to receive a container of an agent, the reusable part reusable for a plurality of diagnostic tests, a disposable part detachably attached to the reusable part and comprising a sample collector to collect a target sample, wherein the disposable part further comprises a sensor to measure a characteristic of the target sample; and a tester comprising a channel to transport the agent to combine the agent and the target sample to form a fluid combination, and to use the fluid combination to diagnose a condition of the target sample.

* * * * *